(12) United States Patent
Maniak et al.

(10) Patent No.: US 7,937,151 B2
(45) Date of Patent: May 3, 2011

(54) IMPLANTABLE MEDICAL DEVICE WITH EMBEDDED PROGRAMMABLE NON-VOLATILE MEMORY

(75) Inventors: Jeremy Maniak, Columbia Heights, MN (US); William L. Zimmer, Roseville, MN (US); Ron A. Balczewski, Bloomington, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 743 days.

(21) Appl. No.: 11/276,490

(22) Filed: Mar. 2, 2006

(65) Prior Publication Data
US 2007/0208261 A1 Sep. 6, 2007

(51) Int. Cl.
*A61N 1/08* (2006.01)

(52) U.S. Cl. ............................................ 607/30; 607/59

(58) Field of Classification Search ..................... 607/30, 607/59; 365/185.29
See application file for complete search history.

(56) References Cited

U.S. PATENT DOCUMENTS

2006/0064149 A1* 3/2006 Belacazar et al. ............ 607/122
2007/0091687 A1* 4/2007 Armstrong et al. ...... 365/185.29

OTHER PUBLICATIONS

Tyson, Jeff "How Flash Memory Works." http://electronics.howstuffworks.com/flash-memory.htm/printable; Jun. 21, 2003.*
Wong, B., et al., "Basics of Design—Embedded Flash Memory", *Electronics Design* (Supplement), (Mar. 15, 2004),8 pgs.

* cited by examiner

*Primary Examiner* — Eric D. Bertram
(74) *Attorney, Agent, or Firm* — Schwegman, Lundberg & Woessner, P.A.

(57) ABSTRACT

A system comprising an implantable medical device (IMD). The IMD includes a processor fabricated on an integrated circuit chip (IC), a random access memory (RAM) circuit fabricated on the same IC, and a programmable non-volatile memory (PNVM) circuit also fabricated on the same IC.

28 Claims, 6 Drawing Sheets

US 7,937,151 B2

IMPLANTABLE MEDICAL DEVICE WITH EMBEDDED PROGRAMMABLE NON-VOLATILE MEMORY

TECHNICAL FIELD

The field generally relates to implantable medical devices and, in particular, but not by way of limitation, to systems and methods for monitoring mechanical activity of the heart.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable insulin pumps, devices implanted to administer drugs to a patient, or implantable devices with neural stimulation capability. IMDs often include microcontrollers or microprocessors along with memory to store information such as program instructions and data. The present inventors have recognized a need for improved performance, life, and reliability of IMDs.

SUMMARY

This document discusses, among other things, systems and methods for monitoring mechanical activity of the heart. A system example includes an implantable medical device (IMD). The IMD includes a processor fabricated on an integrated circuit chip (IC), a random access memory (RAM) circuit fabricated on the same IC, and a programmable non-volatile memory (PNVM) circuit also fabricated on the same IC.

A method example includes providing a programmable non-volatile memory (PNVM) circuit fabricated together with a processor on an integrated circuit chip (IC) in an implantable medical device (IMD), partitioning the PNVM circuit into a plurality of portions based on how often that the processor accesses a portion, and selectively providing power to one or more of the portions according to how often that the processor accesses a portion.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

Figure 1:
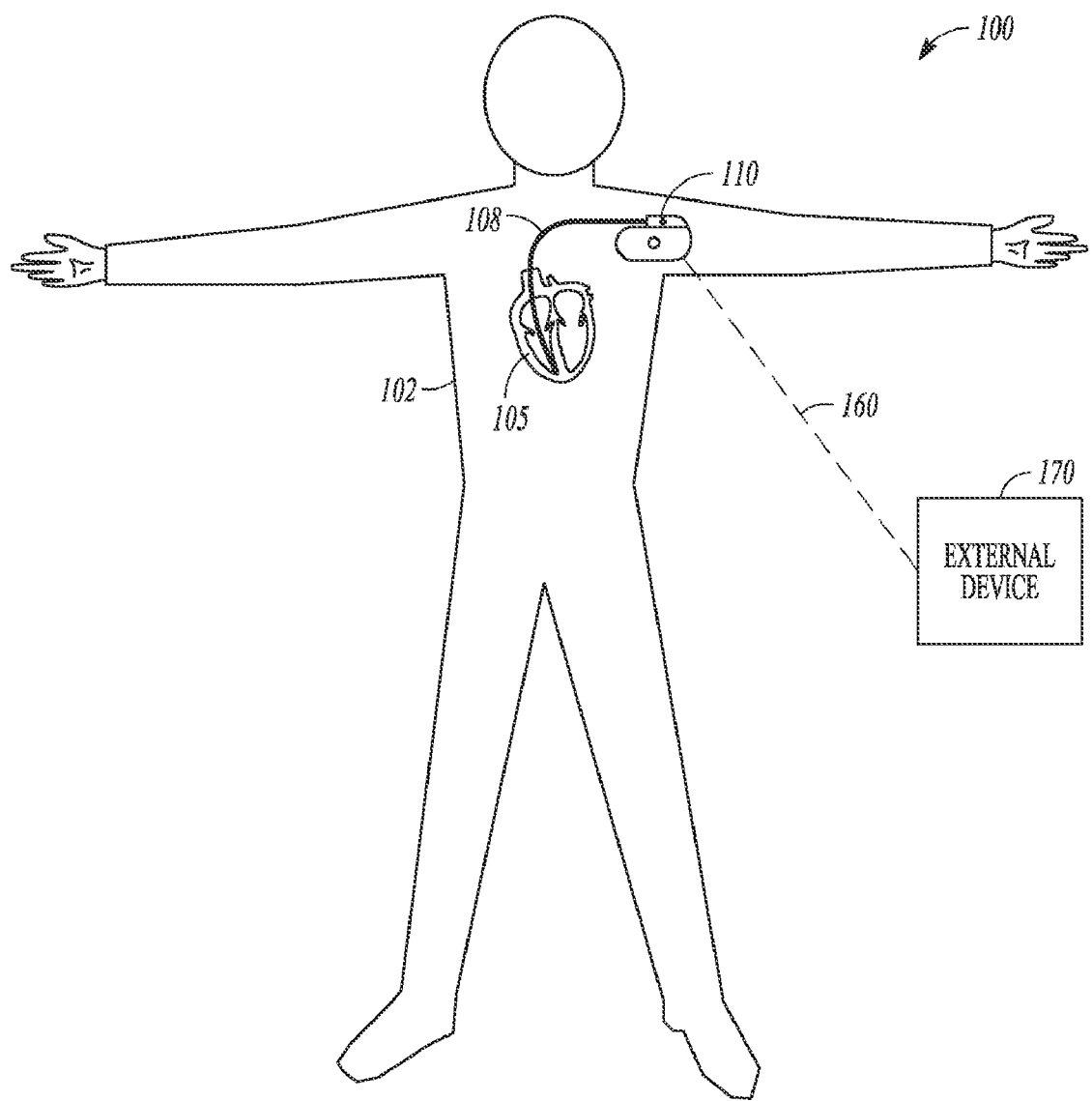
FIG. 1 is a block diagram of portions of a system that uses an implantable medical device (IMD).

FIG. 1 is a block diagram of portions of a system 100 that uses an implantable medical device (IMD) 110. As one example, the system 100 shown is used to treat a cardiac arrhythmia. The IMD 110 typically includes an electronics unit coupled by a cardiac lead 108, or additional leads, to a heart 105 of a patient 102, or otherwise associated with the heart 105. Examples of IMD 110 include, without limitation, a pacer, a defibrillator, a cardiac resynchronization therapy (CRT) device, or a combination of such devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing intrinsic or other electrical activity of the heart 105.

Figure 2:
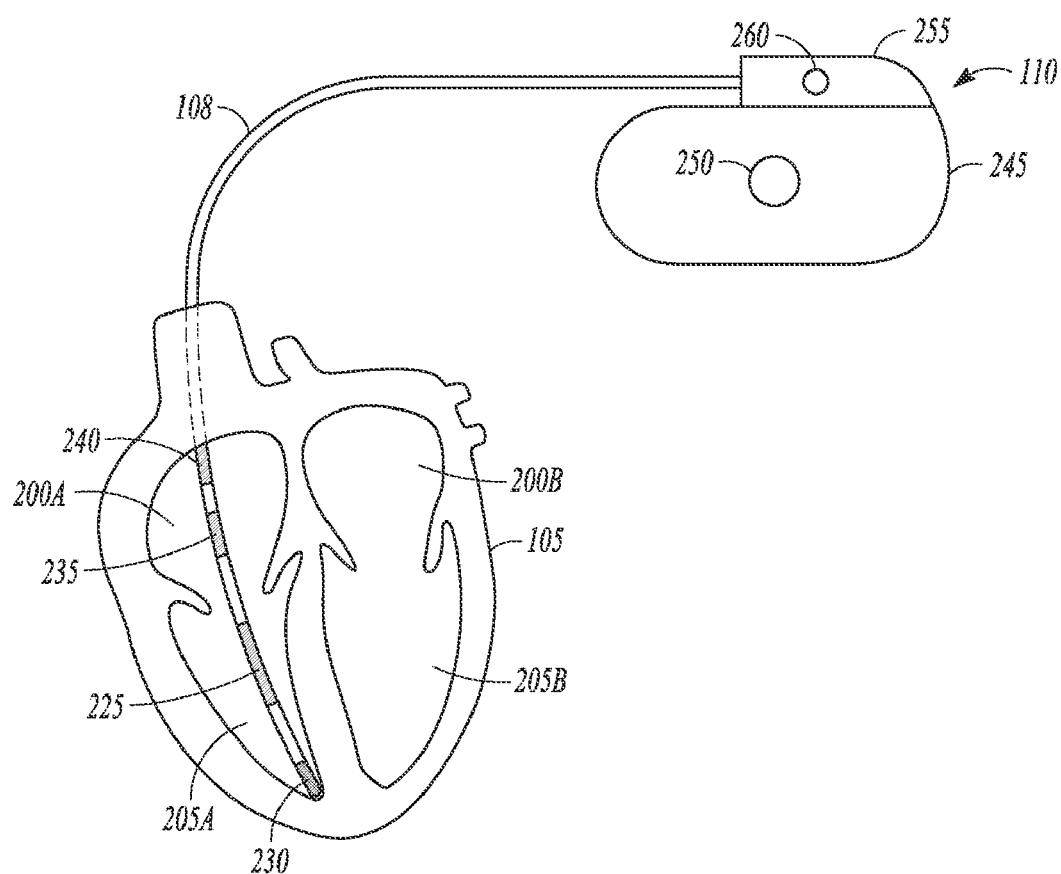
FIG. 2 is an illustration of portions of an IMD coupled by one or more leads to a heart.

FIG. 2 illustrates an IMD 110 coupled by one or more leads 108 to heart 105. Heart 105 includes a right atrium 200A, a left atrium 200B, a right ventricle 205A, and a left ventricle 205B. Lead 108 includes electrodes (electrical contacts, such as ring electrode 225 and tip electrode 230) disposed in a ventricle 205A of heart 105 for sensing signals, or delivering pacing therapy, or both, to the ventricle 205A. Lead 108 also includes one or more electrodes for placement in the right atrium 200A, such as ring electrode 235 and ring electrode 240, for sensing signals, delivering pacing therapy, or both sensing signals and delivering pacing therapy. Sensing and pacing allows the IMD 110 to adjust timing of the chamber contractions. For example, IMD 110 can adjust the timing of ventricular contractions with respect to the timing of atrial contractions delay by sensing a contraction in the right atrium 200A and pacing the right ventricle 205A at the desired AV delay time. The IMD also includes can electrode 250 formed on the IMD can 245, and header electrode 260 formed on the IMD header 255.

IMD optionally also includes additional leads and electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Optionally, lead 108 includes two leads containing two electrodes each. In an example, a first lead includes a tip electrode located in the apex of the right ventricle 205A and a first ring electrode located proximal to the tip electrode. A second lead includes a tip electrode located in the right atrium 200A and a ring electrode located in the right atrium 200A proximal to the tip electrode.

Optionally, IMD 110 includes an additional cardiac lead that includes ring electrodes for placement in a coronary vein extending along a wall of the left ventricle 205B. A lead placed in the left ventricle 205B and a lead placed in the right ventricle 205A may be used to optionally provide resynchronization therapy to the heart 105.

Figure 3A:
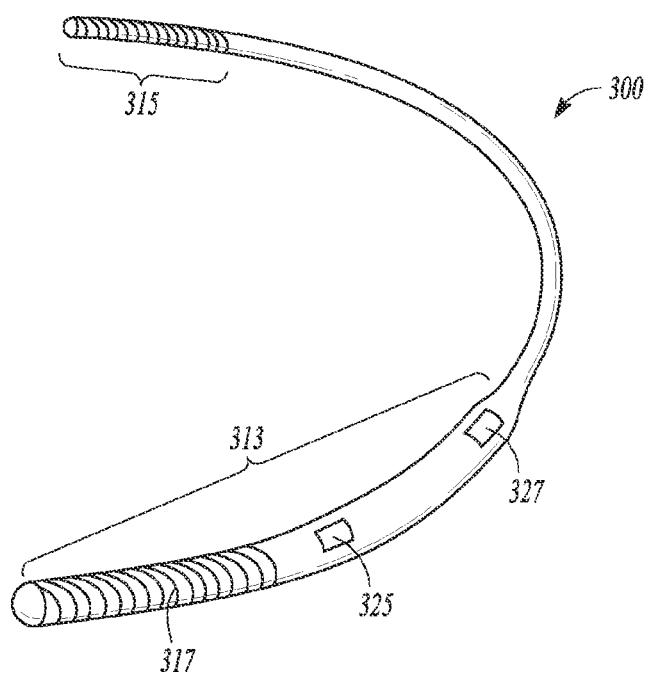
FIGS. 3A-B show an example of an IMD that does not use intravascular leads to sense cardiac signals.
Figure 3B:
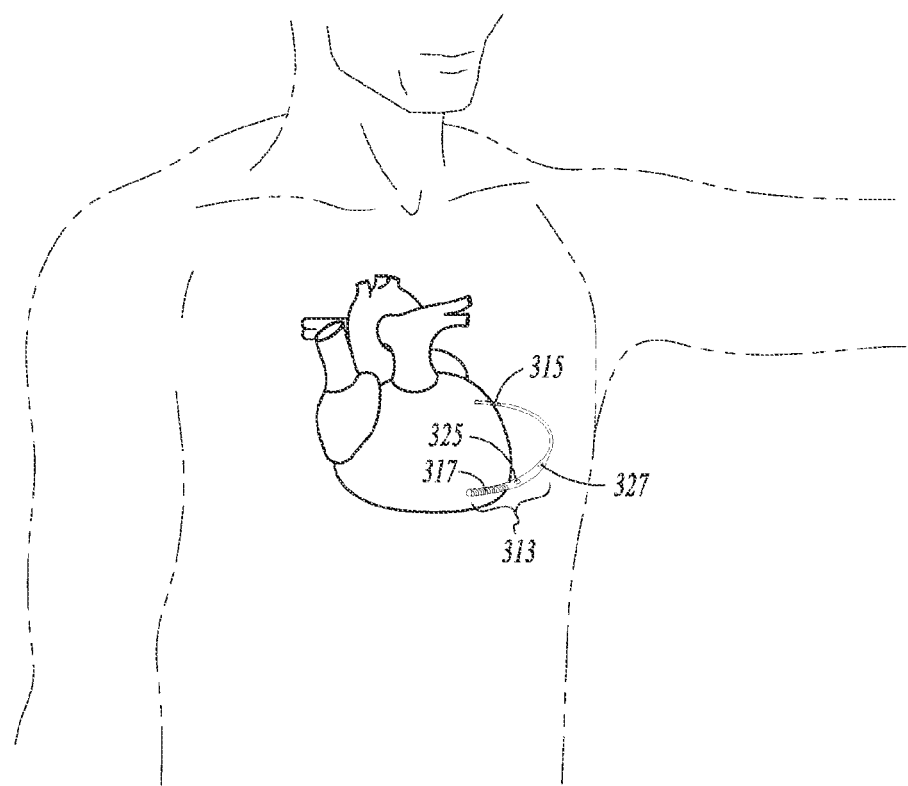

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes. FIGS. 3A-B show an example of an IMD 300 that does not use intravascular leads to sense cardiac signals. FIG. 3A shows that the IMD 300 includes a thicker end 313 to hold the power source and circuits. The IMD 300 also includes electrodes 325 and 327 for remote sensing of cardiac signals. Cardioversion/defibrillation is provided through electrodes 315 and 317. FIG. 3B shows an example of the positioning of the IMD 300 within a patient.

In the past, IMDs were more simple devices and development of firmware executable by a processor in the IMDs was a relatively smaller development effort. In simpler devices, firmware typically becomes stable early in the development cycle and typically is provided in mask ROM. As IMDs continue to become more complex as more functions are added to the devices, designers of IMDs face more challenges in IMD development. Programmable Read Only Memory (PROM) provides some flexibility to firmware development. However, because IMDs are typically battery powered, adding components such as separate processor and PROM may adversely impact battery life. Also, the additional printed circuit board (PCB) interconnect needed when using additional components may negatively impact reliability of a device.

Figure 4:
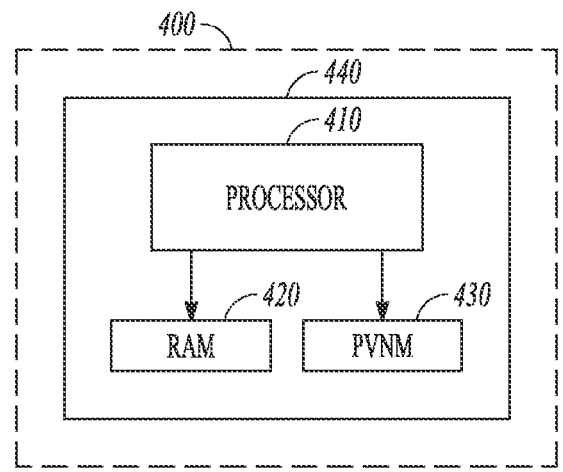
FIG. 4 shows a block diagram of portions of an IMD.

FIG. 4 shows a block diagram of portions of an IMD 400. In this example, the IMD 400 includes a processor 410, a random access memory (RAM) circuit 420, and a programmable non-volatile memory (PNVM) circuit 430, all fabricated on one integrated circuit chip (IC) 440. Because the RAM 420 and the PNVM 430 are fabricated on the same IC 440 as the processor 410, they can be referred to as embedded RAM and embedded PNVM.

In some examples, RAM 420 includes embedded static random access memory (SRAM). In some examples, RAM 420 includes embedded dynamic random access memory (DRAM). In some examples, RAM 420 includes embedded magnetic random access memory (MRAM). In some examples, PNVM 430 includes embedded electrically erasable programmable read only memory (EEPROM). In some examples, PNVM 430 includes embedded flash memory.

PNVM 430 and RAM 420 are typically in communication with the processor 410. In some examples, the IMD 400 includes a bus on the IC 440, and the processor 410 communicates with the memories 420, 430 using the bus. In some examples, processor 410 is a microprocessor. In some examples, processor 410 is a digital signal processor (DSP). In some examples, processor 410 is a controller or microcontroller used to control a process. In the case of the IMD 400, this includes controlling one or more peripheral devices. In some examples, processor 410 is a sequencer. A sequencer refers to a state machine or other circuit that sequentially steps through a fixed series of steps to perform one or more functions. The steps are typically implemented in hardware or firmware.

In some examples, the IMD 400 includes a non-programmable read only memory (ROM) circuit, such as mask ROM, which is fabricated on the IC 440 and is in communication with the processor 410. In some examples, the IMD 400 includes memory that is external to the IC 440 in addition to memory that is embedded with the processor 410 on the IC 440. As an illustrative example, the PNVM 430 and the RAM 420 are embedded with the processor 410 and the ROM is external to the IC 440.

Using PNVM 430 and RAM 420 that reside on the same IC 440 as the processor 410 reduces the cost associated with PCB and reduces the pin count of IMD 400 thereby improving reliability. Providing the memory 420, 430 and processor on a single IC reduces the area required by a processor/memory system. In some examples, the gate feature length of such an IC is 0.18 microns or less. Additionally, having the memory 420, 430 and processor 410 on the same IC reduces the power consumption associated with powering an additional separate IC. This is desirable in battery powered IMDs as it extends the useful life of such devices. To further reduce power consumption, some examples of the IMD 400 selectively supply power to all or one or more portions of the PNVM 430, the RAM 420, or both the PNVM 430 and the RAM 420. In some examples, the IMD 400 selectively adjusts a voltage level or power level to all or one or more portions of the PNVM 430, the RAM 420, or both the PNVM 430 and the RAM 420. This allows the IMD 400 to supply a level of power or voltage to a particular portion that is low enough to place the portion in an inactive state, which does not allow reading or writing to the portion but is sufficient for the portion to retain its stored contents. The IMD 400 supplies a level of power or voltage that is high enough to place a particular portion in its active state (e.g. to enable the portion) when access for reading or writing to the portion is desired.

Figure 5:
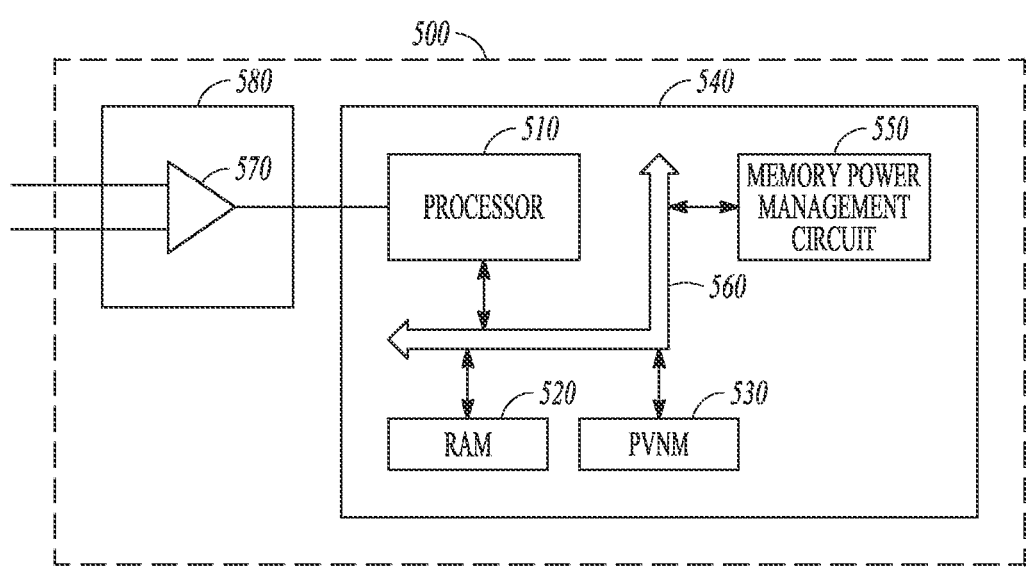
FIG. 5 shows another block diagram of portions of an IMD.

FIG. 5 shows a block diagram of portions of an IMD 500 that includes a processor 510, RAM 520, PNVM 530 and a memory power management circuit 550 to selectively supply or enable power to one or more portions of the PNVM 530 and the RAM 520. The processor 510, RAM 520, PNVM 530 and memory power management circuit 550 are fabricated on the same IC 540. In the example shown, the processor 510, RAM 520, PNVM 530 and the memory power management circuit 550 communicate using a bus 560 on the same IC 540, but this is not necessary. For example, memory power management circuit 550 could be connected directly to PNVM 530 and RAM 520.

Because PNVM 530 retains its contents when power is removed, PNVM can be powered down when access to its contents is not needed. RAM 520 loses its contents when power is removed, so this memory can be powered down using the memory power management circuit 550 when its contents are no longer needed. Alternatively, the power level can be reduced to inactivate, or disable, the RAM 520 but still allow the contents of the RAM 520 to be retained. This allows the RAM 520 to be disabled when it is not desired to access the contents.

IMD 500 also includes one or more intrinsic physiologic signal sense amplifier circuits 570. The intrinsic physiologic signal sense amplifier circuit 570 is coupled to an implantable sensor (not shown) that is either internal to the IMD 500 or is coupled external to the IMD, such as by one or more implantable leads. The sensor or sensors allow for internal monitoring of one or more physiologic parameters of a patient. The intrinsic physiologic signal sense amplifier circuit 570 provides one or more signals to the processor that are representative of such physiologic parameters. In some examples, the intrinsic physiologic signal sense amplifier circuit 570 is fabricated on a separate IC 580 from the processor 510, RAM 520, PNVM 530 and memory power management circuit 550. This allows the IC 540 with the processor to be a purely digital IC. In some examples, the intrinsic physiologic signal sense amplifier circuit 570 is fabricated on the same IC 540. In such an example, the IC 540 is typically a mixed signal IC, i.e. the IC 540 contains a mix of digital and analog electronic circuits.

Examples of the implantable sensors include an accelerometer to monitor patient activity, a pressure sensor to monitor patient blood pressure, and one or more electrodes to monitor electrical heart activity of a patient or to measure intracardiac impedance of a patient. These implantable sensors are often part of an IMD that is a cardiac function management (CFM) device.

In some examples, the one or more intrinsic physiologic signal sense amplifier circuits 570 is coupled to a sampling circuit and an analog to digital converter (A/D) circuit. This allows a signal provided by an intrinsic physiologic signal sense amplifier circuit 570 to be digitized and stored in IMD memory. As an illustrative example, the intrinsic physiologic signal sense amplifier circuit 570 provides a signal representative of electrical heart activity of a patient, and the signal is digitized to provide internal electrograms of the patient which are stored in IMD memory. In some examples, the intrinsic physiologic signal sense amplifier circuit includes a digital signal processor (DSP) fabricated on the same IC 540.

In some examples, information is allocated to RAM 520 and PNVM 530 according to how often the information is accessed by the processor 510. Typically, there are four categories or types of information to be stored in the IMD 500; program code, program variables, critical parameters and variables, and sensor data.

Program code can be partitioned into one or more portions based on how often the processor 510 needs to access the code. If the IMD includes ROM, code that is stable early in the product development cycle is typically stored in ROM. This code can also be partitioned between PNVM 530 and RAM 520. Developing executable program code for IMDs is typically an iterative process. Code that is stable early in development and is accessed less frequently than other code can be stored in PNVM 530 while code accessed more frequently can be stored in RAM. Program code that is stable relatively late in development of the IMD 500 can be stored in PNVM 530 and RAM 520 due to the memories' flexibility. Code accessed less frequently can be stored in PNVM 530 and code accessed more frequently can be stored in RAM 520. The term "portion" can refer to either a memory address range in a memory, or a physically different memory. Thus, two different portions can be either two different memory ranges in a single memory or two portions in two physically different memories.

The flexibility of PNVM 530 permits updating code in the field. This allows for in-field upgrading of program code. For example, if the PNVM 530 is a flash memory, writing or erasing a flash memory cell typically involves providing a voltage sufficient to move electrons across an oxide layer that separates a substrate and a floating gate. The programming can be done in a single pulse, but this may cause minor damage to a cell. Higher programming voltages may allow a cell to be programmed faster, but this may also lead to damage of the cell. A typical approach is to use a series of short pulses to program the flash memory cell.

In some examples, the IMD 500 includes a voltage generator circuit coupled to the PNVM circuit 530 and fabricated on the same IC 540. The voltage generator circuit provides a write voltage and an erase voltage to the PNVM 530. In some examples, the voltage generator circuit includes a charge pump circuit. In some examples, the voltage generator circuit includes a voltage boost converter circuit.

In some examples, programming the PNVM 530 is done under program control of the processor 510. The program code to write the PNVM 530 can be stored in ROM. If the PNVM 530 is partitioned so that an erase and/or write voltage can be provided to some partitions and not others, program code to write a first portion of the PNVM 530 can be stored in a second portion of the PNVM 530. An advantage of using program control is that it requires less hardware than other methods. However, it requires system resources and system interrupts that could complicate the programming process.

In some examples, programming the PNVM 530 is done using a dedicated state machine located on the same IC 540. An advantage of using a dedicated state machine is that the programming of the PNVM 530 can be done in parallel with the processor executing. Code updated in the field that is accessed more frequently can be stored in RAM 520 and code updated in the field that is accessed less frequently can be stored in PNVM 530. Typically, the instruction pointer of the processor is updated to provide access to program code distributed in ROM, RAM 520, and PNVM 530.

The second category of information to be stored in the IMD 500 is program variables. Typically, program variables include data that is frequently used, such as continuously or almost continuously. An example is a memory location used to hold an intermediate calculation. If the IMD 500 is a CFM device, the program variables typically also include data that changes during a cardiac cycle or after several cardiac cycles. Because of the frequency with which they are accessed, program variables are typically stored in RAM 520. In some examples, the program variables are stored in a cache memory implemented in RAM 520.

The third category of information is critical parameters and variables and manufacturing data. This includes information that cannot or should not be lost if power is removed from the IMD 500 or interrupted. Examples of critical parameters and variables include hardware circuit trim information that is used to adjust or trim voltage references, current references, and to trim oscillator frequencies. This information is typically stored in the PNVM 530. Another example is system fault information. System fault information includes an indication, such as a code stored in memory, that a power fault occurred, an indication that a cyclic redundancy code (CRC) error occurred, an indication that a watchdog timer expired, or the like. The system fault information is typically stored in a portion of PNVM 530. In some examples, the portion of a PNVM 530 can be sufficient to hold a code, such as a word of memory, that provides system fault information. In some examples, the portion can be sufficient to hold an "image" or "snapshot" of all or a fraction of processor registers or of cache memory at the time a system fault is detected, thereby providing "state" information associated with the occurrence of system fault.

Examples of manufacturing data includes numbers or letters related to a part or a partial or finished assembly. These numbers can include part numbers, lot numbers, traveler numbers, serial numbers, or the like. The manufacturing data can be stored in the PNVM 530 at an integrated circuit (IC) wafer fabrication facility, at the die packaging facility, or at the IMD manufacturer's facility during various testing stages of device manufacture such as tab test, hybrid assembly test, or final assembly test.

The fourth category of information is sensor data. This typically includes digitized sensor data obtained from one or more signals provided by one or more physiologic sensors and stored for later retrieval. Because access to the sensor data is typically not often required, the sensor data can be stored in PNVM 530, which can be powered down when the sensor data is not being stored or retrieved.

In some examples, the memory power management circuit 550 is configured to supply power to at least one portion of the PNVM 530 substantially only when such portion is accessed by the processor 510. In some examples, the memory power management circuit 550 is configured to provide a power or voltage level to enable the portion of the PNVM 530 substantially only when such portion is accessed by the processor 510. In some examples, certain portions of program code may only need to be used when certain events occur. This allows the portion of memory holding the particular portion of program code to be powered down until it is needed. As an illustrative example, a portion of PNVM 530 containing program code used to sample and store one or more digitized signals obtained from one or more intrinsic physiologic signal sense amplifier circuits 570 can be powered down until a request to obtain such information is generated by the processor 510 or triggered by a physiologic event. For example, a physiologic event detected on one sensor may cause the memory power management circuit 550 to supply power to a partition with program code used to sample signals from one or more other sensors. In some examples, certain portions of PNVM 530 for storing data may only need to be powered up when data is stored in the portion or retrieved from the portion.

In some examples, the memory power management circuit 550 is configured to supply power to a portion of the PNVM 530 according to how often the portion is actually or expected to be accessed by the processor 510. Thus, in this example, the memory power management circuit 550 provides power to a portion of PNVM 530 occasionally or periodically. For example, if a portion of PNVM 530 is used to store data periodically or to read data periodically then power is supplied to the portion of PNVM 530 according to the period of time, such as hourly, daily, weekly, etc. . . .

Therefore, it is also useful to partition program code stored in the memory not only according to the development cycle as discussed above but also or instead according to the function of the program code. Partitioning in this way allows for the ability to supply power to a portion, or supply power or a voltage level to enable a portion, of program code only when its function is needed. For example, a memory storing program code used to implement cardiac function management would typically (depending on the function) always be supplied power. Memory storing program code that implements less-critical functions only need to be supplied power when that function is requested. Examples of code implementing less-critical functions include code used to obtain electrograms or telemetry code used for communication with an external device.

It is also useful to partition data according to the type or category of information to be stored in the portions. Partitioning in this way allows for the ability to supply power to a portion, or supply a voltage level to enable a portion, of the memory only when the type of data is needed. For example, power could be continuously supplied to a memory portion storing critical parameters and variables, but only supplied to a portion to store sensor data when such sensor data is to be stored or read. This allows an IMD 500 to acquire sensor data, store it in a portion of PNVM 530, remove power from that portion to preserve battery energy, and then provide power to the PNVM 50 when it is desired to use the sensor data, such as to transmit the sensor data to an external device, for example.

In some examples, the IMD 500 includes a communication circuit coupled to the processor and the IMD 500 is part of a system that includes an external device configured to communicate with the IMD 500. In some of the examples, the communication circuit is on the same IC 540 as the processor and in some of the examples the communication circuit is on a separate IC. In certain examples, the PNVM 530 is configured to store a module including telemetry code performable by the processor 510 to communicate information wirelessly with the external device. In some of the examples, power is supplied to the portion storing the module when the IMD detects a transmission signal from an external device.

In some examples, the external device is configured to download performable code into the IMD 500, such as for storage in the PNVM 530 and to be performed by the processor 510, and the module stored in the PNVM 530 is configured to receive the performable code for storage in the PNVM 530. In some examples, an update module is stored in a first portion of the PNVM 530. The update module is configured to rewrite one or more executable instructions stored in a second portion of the PNVM 530. In some examples, the rewrite originates from the external device and the external device downloads performable code. In some examples, the rewrite originates from the IMD 500.

In some examples, program code modules or data modules are stored or installed in the PNVM 530 at a manufacturer's facility. In some examples, modules are updated in the PVNM 530 in the field.

In some examples, the external device is an IMD programmer. In some examples, the external device includes a computer in communication with a network such as a hospital computer network or the Internet. In some examples, the IMD 500 communicates with an advanced patient management (APM) system in which the external device includes a remote server connected to a network. The remote server typically communicates wirelessly with the IMD 500 using a repeater. This is useful for, among other things, automatic updating of program code or program variables in the IMD 500, such as from a remote server that is located in a facility associated with the IMD manufacturer or a clinic.

In some examples, an error detection module is stored in a first portion of the PNVM 530. The error detection module is configured to detect one or more errors in at least a second portion of the PNVM 530. This is useful for checking the integrity of program code that is altered or downloaded into the IMD 500, such as into the second partition of the PNVM 530. The code stored in the second portion of the PNVM 530 is not executed if the integrity check fails. In some examples, the error detection module performs a CRC check of the program code in the second portion of the PNVM 530. In some examples, parity bit checking is used to detect errors such as by providing a parity bit for a block or page of memory. In some examples, the error detection module includes an error correction module configured to correct one or more errors in the second portion of the PNVM 530. In some examples, the error correction module uses a Modified Hamming Code to detect and correct errors in the second portion of the PNVM 530.

In some examples, the IMD 500 includes at least one output to administer a substance and a control circuit coupled to the at least one output and the processor 510. The control circuit is configured to control delivery of the substance. In some examples, the IMD 500 the substance is a drug and the MD 500 provides drug therapy, such as part of cardiac function management. In some examples, the IMD 500 instead or also provides electrical therapy.

Figure 6:
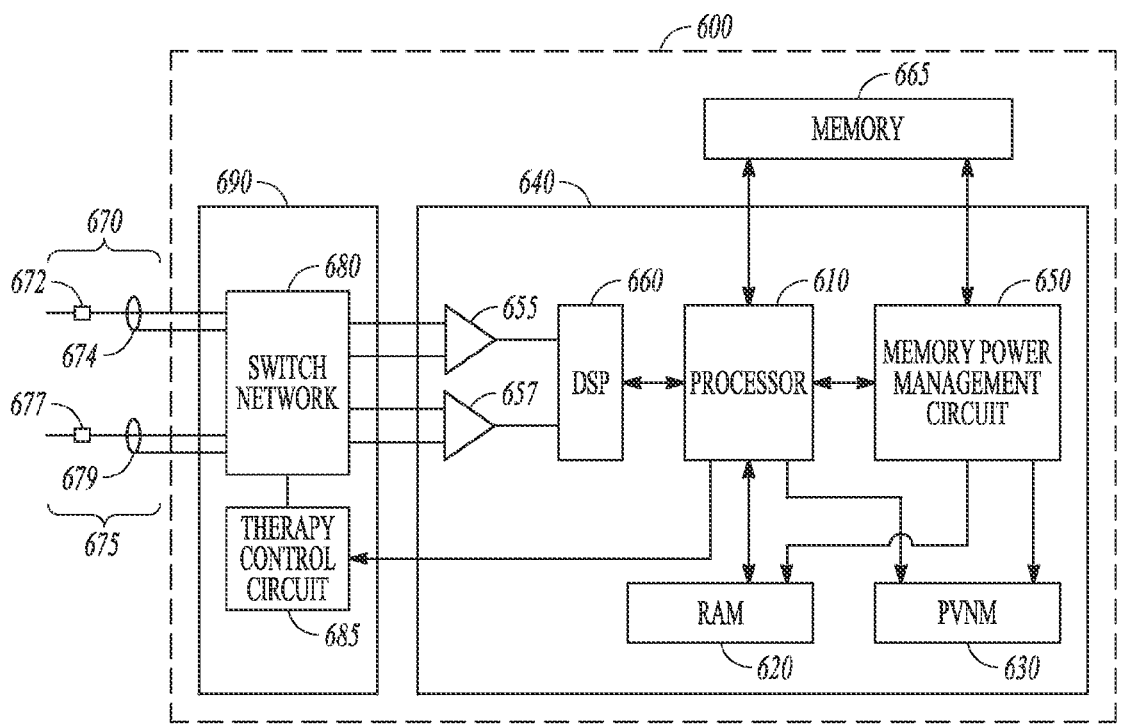
FIG. 6 shows another block diagram of portions of an IMD.

FIG. 6 shows a block diagram of portions of an IMD 600 that includes a processor 610, RAM 620, PNVM 630, and a memory power management circuit 650 fabricated on a single IC 640. The IMD 600 also includes first and second sense amplifiers 655, 657 and DSP 660 fabricated on the same IC 640. Memory power management circuit 650 selectively supplies power, or enabling power, to one or more portions of RAM 620, one or more portions of PNVM 630, or one more portions of memory 665 external to the IC 640. In some examples, the external memory 665 includes ROM, RAM, PNVM or any combination including two or more of ROM, RAM, or PNVM.

In certain examples, the IMD 600 is a cardiac function management (CFM) device. The IMD 600 typically includes first and second cardiac leads 670, 675 that typically include tip electrodes 672, 677 and ring electrodes 674, 679. The leads 670, 675 are typically coupled to sense amplifiers 655, 657, such as through switch network 680. The electrodes 672, 674, 677, and 679 are typically shaped and sized for placement on or near portions of a heart to provide sensing of electrical activity of the heart. The IMD 600 also typically provides electrostimulation or countershock using the leads 670, 675. The IMD 600 typically includes therapy control circuit 685 to control delivery of the electrostimulation or countershock electrical therapy. The switch network 680 allows electrical signals from either lead 670, 675 to be sensed by either sense amplifier 655, 657. The switch network 680 also allows for electrical isolation of the sense amplifiers 655, 657 from the leads 670, 675 during therapy. In the IMD 600 shown, the switch network 680 and therapy control circuit 685 are provided on an IC 690 that is different from the IC 640 containing the processor 610 and the PNVM 630. This prevents damage to the IC 640, such as if the electrical therapy provides a voltage that exceeds the rating of the IC 640.

Figure 7:
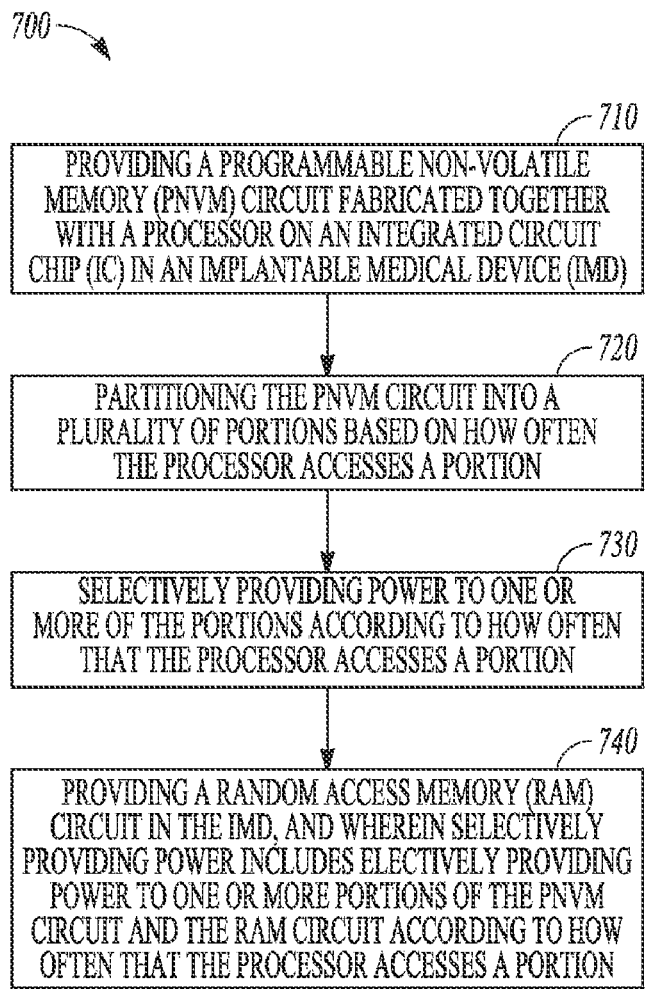
FIG. 7 shows a block diagram of a method of managing energy used by an IMD.

FIG. 7 is a block diagram of a method 700 of managing energy used by an IMD. At 710, a programmable non-volatile memory (PNVM) circuit fabricated together with a processor on an integrated circuit chip (IC) is provided in an implantable medical device (IMD). At 720, the PNVM circuit is partitioned into a plurality of portions, such as based on how often the processor accesses a particular portion, or how often it is expected to access that portion. The term "portion" includes either a memory address range in a memory, or a physically different memory. At 730, power is selectively provided or enabled to one or more of the portions, such as according to how often that the processor accesses or is expected to access a portion. In some examples, power is selectively provided to one or more of the portions substantially only when such portion is accessed by the processor. The ability to selectively power-down circuits in an IMD, such as memory circuits, reduces the drain of energy from a battery. This extends the life of a battery-powered IMD. Energy drain from a battery is also reduced by providing a low level of power to disable the portion of the memory circuits. The portion of the memory circuits can then be re-enabled by restoring power to an adequate level. Placing the processor and the memory on the same IC further reduces battery energy consumption in that having less individual ICs requires less power, and reduces interconnect between the ICs, also resulting in requiring less power.

In some examples, the method 700 further includes, at 740, providing a random access memory (RAM) circuit in the IMD. In certain examples, selectively providing power includes selectively providing power to one or more portions of the PNVM circuit and the RAM circuit, such as according to how often that the processor accesses a particular portion of the PNVM circuit or the RAM circuit. In some examples, the method 700 includes providing a non-programmable read only memory (ROM) circuit, and the selectively providing power includes selectively providing power to one or more portions of the PNVM circuit, the RAM circuit, and the ROM circuit, such as according to how often that the processor accesses a portion of the PNVM circuit, the RAM circuit, and the ROM circuit.

In some examples, the method 700 includes storing an update module in a first portion of the PNVM circuit. The update module typically includes processor performable instructions to effect rewriting of one or more performable instructions stored in a second portion of the PNVM circuit. In some examples, the method 700 includes downloading blocks of instructions to the IMD, and performing at least one integrity test on a downloaded block of instructions before allowing the processor access to the downloaded block of instructions. In some examples, performing an integrity test includes performing an error detection test. In some examples, performing the error detection test includes calculating a cyclic redundancy code (CRC) over one or more blocks of memory. In some examples, performing an integrity test includes performing error detection and correction. In some examples, performing error detection and correction includes using a Modified Hamming Code to detect or correct errors.

The systems and methods described herein improve reliability of IMDs by reducing interconnections between IMD functional blocks. Power required to operate the IMD is also reduced by reducing the number of integrated circuits in an IMD. Power consumption can be reduced further by selectively powering down memory that exists on the same IC as a processor of the IMD, or by powering down memory external to the IC.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   an implantable medical device (IMD) comprising:
   a processor fabricated on an integrated circuit chip (IC);
   a random access memory (RAM) circuit, fabricated on the same IC;
   a programmable non-volatile memory (PNVM) circuit, fabricated on the same IC, wherein the PNVM circuit and the RAM circuit are in communication with the processor, and wherein the PNVM circuit is partitioned, prior to storing of information, into a plurality of portions based on a type of information to be stored in a portion; and
   a memory power management circuit fabricated on the same IC and in communication with the processor, wherein the memory power management circuit is configured to selectively provide power or selectively restrict power to one or more portions of the PNVM circuit, and wherein power is selectively provided to one or more of the portions according to the type of information to be stored in the portion.

2. The system of claim 1, wherein the memory power management circuit is configured to selectively adjust power of one or more portions of the RAM circuit between a first level of power to place a portion in an active state and a second level of power to place the portion in an inactive state.

3. The system of claim 2, wherein the memory power management circuit is configured to selectively supply power to the portion.

4. The system of claim 1, wherein the memory power management circuit is configured to supply power to at least one portion of the PNVM circuit substantially only when such portion is accessed by the processor.

5. The system of claim 1, wherein the IMD further includes a non-programmable read only memory (ROM) circuit in communication with the processor.

6. The system of claim 5, wherein the ROM circuit is fabricated on the same IC.

7. The system of claim 1, further including a voltage generator circuit coupled to the PNVM circuit and fabricated on the same IC, to provide a write voltage and an erase voltage to the PNVM circuit.

8. The system of claim 7, wherein the PNVM circuit includes a first portion that includes an update module, wherein the update module is configured to rewrite one or more executable instructions stored in a second portion of the PNVM circuit.

9. The system of claim 1, wherein the PNVM circuit includes a first portion that includes an error detection module configured to detect one or more errors in at least a second portion of the PNVM circuit.

10. The system of claim 9, wherein the error detection module includes an error correction module configured to correct one or more errors in the second portion of the PNVM circuit.

11. The system of claim 1, wherein the IMD includes at least one intrinsic physiologic signal sense amplifier circuit, the sense amplifier fabricated on the same IC.

12. The system of claim 11, in which the intrinsic physiologic signal sense amplifier is configured to monitor electrical heart activity of a patient, and wherein a portion of the PNVM circuit is configured to store code to implement cardiac function management.

13. The system of claim 11, wherein the intrinsic physiologic signal sense amplifier circuit is in communication with a sampling circuit, and wherein a portion of the PNVM circuit is configured to store data obtained from the sampling circuit.

14. The system of claim 11, wherein the intrinsic physiologic signal sense amplifier circuit includes a digital signal processor (DSP) fabricated on the same IC.

15. The system of claim 1, wherein the PNVM circuit is configured to store system fault information.

16. The system of claim 1, wherein the PNVM is configured to store hardware circuit trim information.

17. The system of claim 1, wherein the IMD further includes:
    a communication circuit, coupled to the processor; and
    wherein the PNVM circuit is configured to store a module including code performable by the processor to communicate information wirelessly with an external device to receive from the external device performable code for storage in the PNVM circuit and to be performed by the processor.

18. The system of claim 17, comprising an external device configured to communicate with the IMD, and wherein the external device is configured to download performable code into the IMD for storage in the PNVM circuit and to be performed by the processor.

19. The system of claim 1, wherein a gate length feature of the IC is 0.18 micron or less.

20. The system of claim 1, wherein the IMD further includes:
    at least one output, to provide electrostimulation or countershock;
    a control circuit, coupled to the at least one output and the processor, the control circuit configured to control delivery of the electrostimulation or countershock; and
    at least one electrical input to receive sensed electrical activity of a heart.

21. The system of claim 20, wherein the IMD includes a cardiac function management device.

22. The system of claim 1, wherein the IMD further includes:
    at least one output, to administer a substance; and
    a control circuit, coupled to the at least one output and the processor, the control circuit configured to control delivery of the substance.

23. The system of claim 1, wherein the IMD is configured to receive downloaded blocks of instructions and to perform at least one integrity test on a downloaded block of instructions before allowing the processor access to the downloaded block.

24. The system of claim 1, further comprising a non-programmable read only memory (ROM) circuit in the IMD, and wherein the IMD is configured to selectively provide power to one or more portions of the PNVM circuit, the RAM circuit, and the ROM circuit according to the type of information stored in the portion.

25. A system comprising:
an implantable medical device (IMD) comprising:
  a processor fabricated on an integrated circuit chip (IC);
  a random access memory (RAM) circuit, fabricated on the same IC; and
  a programmable non-volatile memory (PNVM) circuit, fabricated on the same IC, wherein the PNVM circuit and the RAM circuit are in communication with the processor, and wherein the PNVM circuit is partitioned into a plurality of portions; and
  a memory power management circuit fabricated on the same IC and in communication with the processor, wherein the memory power management circuit is configured to selectively provide power or selectively restrict power to one or more portions of the PNVM circuit, and supply power to a portion of the PNVM circuit according to how often that portion of the PNVM circuit is accessed by the processor.

26. A system comprising:
an implantable medical device (IMD) comprising:
  a processor fabricated on an integrated circuit chip (IC);
  a random access memory (RAM) circuit, fabricated on the same IC;
  a programmable non-volatile memory (PNVM) circuit, fabricated on the same IC, wherein the PNVM circuit and the RAM circuit are in communication with the processor, wherein the PNVM circuit is partitioned into a plurality of portions based on how often that the processor accesses a portion; and
  a memory power management circuit fabricated on the same IC and in communication with the processor, wherein the memory power management circuit is configured to selectively provide power or selectively restrict power to one or more portions of the PNVM circuit, and power is selectively provided to one or more of the portions according to how often that the processor accesses a portion.

27. The system of claim 26, further comprising providing a non-programmable read only memory (ROM) circuit, and wherein power is selectively provided to one or more portions of the PNVM circuit, the RAM circuit, and the ROM circuit according to how often that the processor accesses a portion.

28. The system of claim 26, comprising an update module in a first portion of the PNVM circuit, the update module configured to rewrite one or more executable instructions stored in a second portion of the PNVM circuit.

* * * * *